United States Patent [19]

Brown

[11] Patent Number: 4,882,741
[45] Date of Patent: Nov. 21, 1989

[54] MULTILEAF COLLIMATOR AND RELATED APPARATUS

[75] Inventor: Kevin J. Brown, Crawley, England

[73] Assignee: U.S. Philips Corporation, New York, N.Y.

[21] Appl. No.: 263,090

[22] Filed: Oct. 26, 1988

[30] Foreign Application Priority Data

Oct. 28, 1987 [GB] United Kingdom ............... 8725253

[51] Int. Cl.⁴ .................................................. G21K 1/04
[52] U.S. Cl. ........................................ 378/152; 378/206
[58] Field of Search ..................... 378/151, 152, 206; 250/505.1

[56] References Cited

U.S. PATENT DOCUMENTS 4,739,173 4/1988 Blosser et al. ..................... 378/152
4,754,147 6/1988 Maughan et al. .................. 378/152

Primary Examiner—Craig E. Church
Attorney, Agent, or Firm—Jack E. Haken

[57] ABSTRACT

A collimating arrangement for use in radiotherapy apparatus has a set of mutually contiguous members (8) for substantially attenuating radiation. The positions of the members (8) are adjustable so that edges (8a) thereof form an adjustable aperture (9) for defining the cross-sectional shape of the beam. A lamp (12) illuminates an area including the beam-defining edges (8a). Each of the members (8) is provided with a respective retroreflector (19) for reflecting illumination from the lamp (12) into the camera (13) substantially independently of the position of the beam-defining edges (8a). A detecting arrangement, including a video camera (13), more responsive to the higher intensity of illumination reflected from the retroreflectors (19) than from respectively adjacent regions in the illuminated area, is used to detect the positions of the retroreflectors (19) which are respectively representative of the positions of the edges of the members.

10 Claims, 2 Drawing Sheets

MULTILEAF COLLIMATOR AND RELATED APPARATUS

The invention relates to a collimating arrangement for a beam of radiation, comprising a set of mutually contiguous members which substantially attenuate said radiation, means for adjusting the positions of the members so that edges thereof form an adjustable aperture for defining the cross-sectional shape of the beam, illuminating means for illuminating an area including the beam-defining edges of said members, and detecting means responsive to spatial variations in the intensity of illumination reaching the detecting means from said area for determining the positions of said beam-defining edges.

The invention further relates to radiotherapy apparatus comprising such a collimating arrangement.

A collimating arrangement as set forth in the opening paragraph is known from EP No. 193 509 A. The specification discloses a multileaf collimator, particularly for radiation therapy equipment using a high-energy beam of penetrating radiation, with an optical system comprising a light bulb to illuminate the irradiated surface, mirrors, and a TV camera which is arranged to "see" the leaf collimator from the effective radiation source. The TV camera establishes the position of each collimator leaf by detecting light/dark transitions in predetermined lines of the TV camera picture. In the arrangement described in detail with reference to FIG. 8 of the drawings which depicts a pair of opposed leaves as seen by the TV camera, the leaves appear dark and the region between the leaves, which forms part of the aperture defining the area to be irradiated by the high-energy beam, appears light. The intensity of illumination seen by the TV camera in the region between the leaves will depend inter alia on the reflectivity of the surface to be irradiated and the ambient and/or illuminating light intensity, and consequently that the contrast between the light and dark areas is variable and is in practice liable to be rather poor so that the determination of the positions of the edges of the leaves may not be reliably accurate. The specification mentions alternatives to the arrangement described in detail, including providing the upper surface of the leaves with a reflective surface reflecting the field light back into the TV camera; it is not clear from the specification how exactly this alternative arrangement would operate, but again the contrast is liable to vary with ambient and/or illuminating light intensity and is likely to be rather poor.

According to the present invention, a collimating arrangement as set forth in the opening paragraph of this specification is characterized in that each of said members is provided with respective retroreflector means for reflecting illumination from the illuminating means into the detecting means substantially independently of the position of said beam-defining edges of said members, and in that the detecting means are more responsive to the higher intensity of illumination reflected from the retroreflector means than reflected from adjacent regions in said area so as to detect the positions of the retroreflector means which are respectively representative of the positions of said edges of said members. Such an arrangement has the advantage over the above-mentioned known arrangement of enabling a much higher level of contrast to be obtained, so that the determination of the positions of the edges of the members can be substantially independent of factors such as the reflectivity of the surface to be irradiated and the intensity of illumination from the illumination means and/or ambient illumination.

The retroreflector means may be mounted on the respective members so providing a relatively simple and accurate arrangement. As an alternative, the retroreflector means may be coupled to the respective members by an appropriate mechanical arrangement, for example by levers.

Each of the retroreflector means, which may for example be a strip of commercially-available retroreflective material, may extend along the respective leaf, i.e. in a direction transverse to the beam-defining edge of the leaf, for most or all of its length so that the detecting means only "see" one edge of the retroreflector means. Preferably, however, each of the retroreflector means is of a limited extent having two opposed edges spaced-apart in a direction transverse to the respective beam-defining edge, and the detecting means are arranged to detect illumination reflected from said two edges of each retroreflector means in said area and to determine therefrom the position of the beam-defining edge of the respective member.

The ability of the detecting means to detect the said two opposed edges of each localized retroreflector means enables the location of the retroreflector means, and thus the position of the beam-defining edge of each member in said area, to be determined more precisely and the detected position to be less liable to vary with the intensity of illumination. The detecting means may be arranged to determine a midpoint between the said two opposed edges of each retroreflector means from the illumination reflected from the said two edges. The detecting means may be arranged to detect when the intensity of reflected illumination passes through a predetermined threshold enabling the position of the said two opposed edges of each retroreflector means, and thus also the position of the said beam-defining edges, to be determined substantially independently of variations in the intensity of illumination due, for example, to aging or to variations in a supply voltage.

The detecting means may have an entrance diaphragm defining an entrance aperture sufficient to allow only illumination from the illumination means reflected by the retroreflector means into the detecting means so facilitating enhancement of the contrast between the retroreflected illumination and illumination reflected by scattering from other surfaces in the said area. The detecting means may comprise a video camera, in which case the iris diaphragm of the video camera can be used as the entrance diaphragm.

A collimator embodying the invention may be used in radiotherapy apparatus comprising means for generating a beam of penetrating radiation, in that case high-energy X-rays or electrons. As an alternative, a collimating arrangement embodying the invention may be used with diagnostic apparatus, for example an X-ray simulator which is intended for use in conjunction with radiotherapy apparatus and which comprises a patient support table and a source of diagnostic X-rays at a position corresponding to the source of high-energy radiation in the radiotherapy apparatus.

In such radiotherapy apparatus, further retroreflector means, that is retroreflector means in addition to the retroreflector means with which the members are provided, may be provided for defining a desired cross-sectional beam shape, the detecting means being arranged to detect illumination from the illumination means reflected by the further retroreflector means to determine the desired cross-sectional beam shape defined by the further retroreflector means, together with means for storing said desired cross-sectional beam shape determined by the detecting means and means for adjusting the positions of said members so that the actual beam shape substantially corresponds to the desired shape. This can be used for setting the apparatus so as to illuminate a desired region of a patient. For example, a set of mutually contiguous further members may be provided for substantially attenuating illumination from the illuminating means, the positions of the further members being adjustable so that edges of the further members form an adjustable aperture defining the cross-sectional shape of the illuminating beam from the illuminating means, the lengths of said aperture-defining edges of the further members respectively subtending the same angles at the illuminating means as the lengths of corresponding beam-defining edges of the members of the first-said set, and each of said further members may be provided with respective further retroreflector means so that the positions of the further retroreflector means are respectively representative of the positions of the aperture-defining edges of the further members, the further retroreflector means being arranged to reflect illumination from the illuminating means into the detecting means. With the patient positioned for treatment, the further (illumination-attenuating) members may be adjusted so that the boundary of the illuminated area on the patient substantially matches an outline drawn on the skin of the patient. The further members need only substantially attenuate the illumination from the illuminating means and can therefore be lighter and more easily movable than the members of the first-mentioned set for substantially attenuating the radiation. The apparent positions of the aperture-defining edges of the further members, i.e. in terms of the angles subtended at the illuminating means, can then be stored and the main set of radiation-attenuating members set to the same positions. As an alternative, the further retroreflector means may be carried by support means adapted to be manually moved along a path defining the desired beam shape, for example the further retroreflector means may be mounted at the end of a stick.

Embodiments of the invention will now be described, by way of example, with reference to the schematic drawings, in which.

Figure 1:
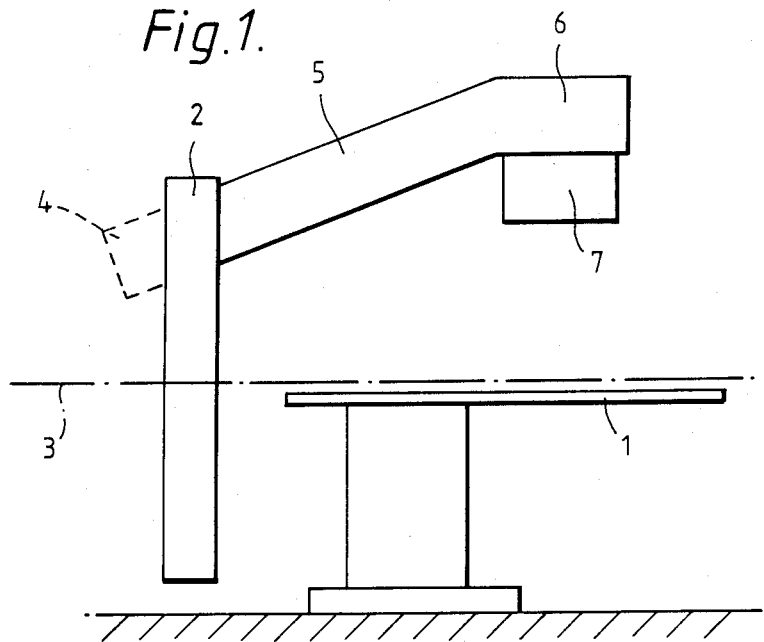
FIG. 1 is a side view showing in outline radiotherapy apparatus comprising a collimating arrangement embodying the invention.

FIG. 1 illustrates apparatus for irradiating a patient with a beam of high-energy electrons or X-rays. The patient is supported on an adjustable table 1. A gantry 2 rotatable through substantially 360° about a horizontal axis 3 supports an electron source 4, a linear accelerator (linac) 5 which accelerates the electrons to a selectable energy typically in the range 4–25 MeV (Mega electron volts), beam-deflection system at 6 which gives the electron beam a net deflection of more than 90 degrees so that the normally towards the axis 3, and a head 7 which comprises means for providing the radiotherapy beam with the desired characteristics and which includes a collimating arrangement embodying the invention. The radiotherapy beam may be the electron beam produced by the linac or may be a beam of high-energy X-rays produced by causing the electron beam to impinge, after deflection at 6, on a suitable X-ray target.

Figure 2:
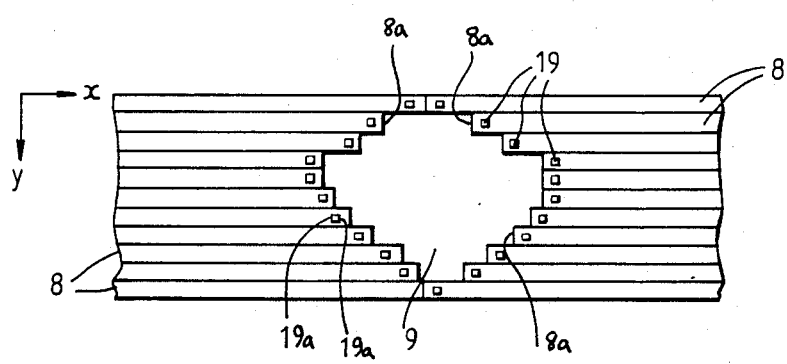
FIG. 2 is a plan view of a multileaf collimator defining the cross-sectional shape of the high-energy beam of radiation.

FIG. 2 is a plan view of a multileaf collimator in the head 7. The collimator comprises a set of parallel mutually contiguous elongate members or leaves 8, arranged in longitudinally opposed pairs. The positions of the leaves 8 are rectilinearly adjustable longitudinally, that is to say in the x-direction indicated in FIG. 2, by means not shown (such as respective electric motors). The material of the leaves 8 and their thickness (their dimension in a direction perpendicular to the plane of FIG. 2, that is in the z-direction) are such that they substantially attenuate the portion of the beam of high-energy radiation that is incident on them. The edge $8a$ of each leaf 8 nearest the longitudinally opposed leaf 8 of the same pair forms a portion of a boundary of an aperture 9 for defining the cross-sectional shape of the beam. The leaves 8 are sufficiently narrow (their y-dimension in FIG. 2) and sufficiently numerous to enable the cross-sectional beam shape to be closely approximated to a desired region to be irradiated on a patient.

Figure 3:
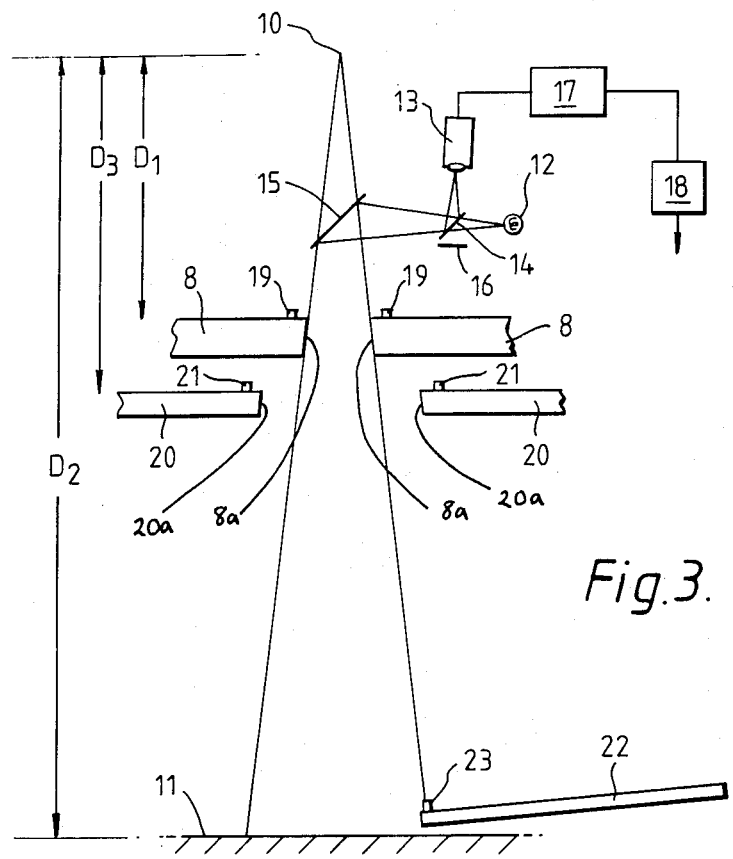
FIG. 3 is a side view of the optical system for determining the positions of the edges of the leaves and a pair of the leaves.

FIG. 3 is a side view of the optical system for determining the positions of the edges of the leaves together with one pair of leaves, FIG. 2 being a view from the side of the collimator facing the incident beam, i.e. from above with respect to the orientation depicted in FIGS. 1 and 3.

As shown in FIG. 3, the location of the effective source of the radiation beam is designated 10. This location is the point at which the deflected beam of electrons derived from the linac 5 is brought to a focus (suitably a focus with respect to both position and velocity); if the radiotherapy beam is to be of X-rays rather than electrons, a suitable X-ray target is disposed at that location. The distance from the source 10 to the collimator leaves 8 is designated $D_1$ and the distance from the source 10 to the region of the patient to be irradiated (for simplicity indicated as a surface 11) is designated $D_2$. An optical system for determining the positions of the beam-defining edges $8a$ of the leaves 8 that bound the aperture 9 comprises an illuminating lamp 12 for illuminating an area including the beam-defining edges $8a$ of the leaves 8, a video camera 13, a semi-transparent mirror 14 and a mirror 15 which is reflective to the illumination from the lamp 12 and which either is substantially transparent to the beam of high-energy radiation or can be moved out of the path of the radiation beam when the latter is in use. The arrangement is such that the lamp 12 and camera 13 are at locations optically substantially corresponding to one another and also to the effective source 10 of the radiation beam. An optically black surface 16 is disposed directly in front of the camera 13 beyond the semi-transparent mirror 14. The camera 13 is connected to video processing and storage means 17, which in turn are connected to control means 18 for adjusting the positions of the leaves 8.

In accordance with the invention, in order to obtain much greater contrast for determining the positions of the beam-defining edges of the leaves 8, each of the leaves 8 is provided with respective retroreflector means $8a$. As shown in FIGS. 2 and 3, the retroreflector means comprise a respective retroreflector 19 mounted on the narrow upper longitudinal side of each leaf 8 facing the illuminating beam. As a result, light from the lamp 12 which is incident on the retroreflectors 19 is reflected back substantially along its incident path, irrespective of the positions of the beam-defining edges 8a of the leaves 8, and approximately half this reflected illumination is directed to the camera 13. Consequently, the camera "sees" a much higher level of illumination reflected from the retroreflectors 19 than reflected from the adjacent regions in the said illuminated area forming its field of view, the latter being light from the lamp 12 reflected or scattered from the upper sides of the leaves 8 and light from the lamp 12 plus ambient illumination scattered from the surface 11. The retroreflectors 19 can thus be unambiguously discerned against the background.

Figure 4:
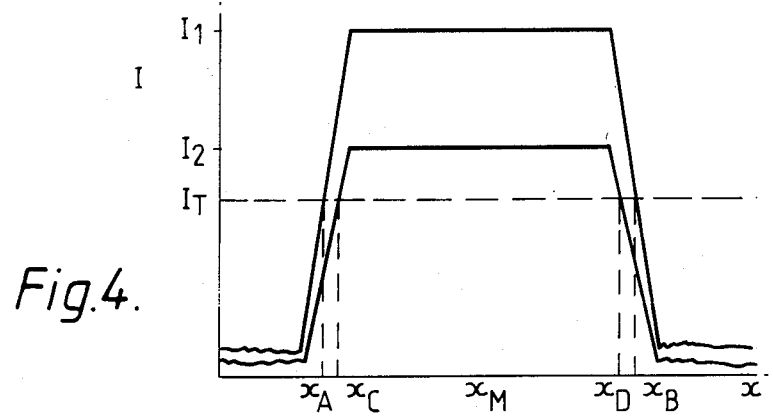
FIG. 4 is a graph of illumination intensity against distance.

In this embodiment, each retroreflector 19 is of limited extent having two opposed edges 19a spaced-apart in a direction transverse to the beam-defining edges 8a of the leaves, i.e. the x-direction. The variation with distance in the x-direction of the intensity I of illumination reaching the camera 13 reflected from the vicinity of a retroreflector 19 is indicated diagrammatically in FIG. 4 for two different levels of illumination from the lamp, giving maximum intensities $I_1$ and $I_2$ respectively reflected from the retroreflector 19. The processing and storage means 17 determine, for each retroreflector in the said area or field of view, positions at which the intensity crosses a threshold value $I_T$, namely $x_A$, $x_B$ with the higher level of illumination and $x_C$, $x_D$ with the lower level so as to provide an indication of the position of the two opposed edges 19a. The processing and storing means 17 then determines a reference point spaced by a predetermined distance from the said two opposed edges 19a, for example a mean or midpoint $x_M$ half-way between the positions $x_A$, $x_B$ or $x_C$, $x_D$ at which the intensity of reflected illumination crosses the threshold value $I_T$. As is apparent from FIG. 4, the value of $x_M$ is independent of the level of illumination. The system is calibrated prior to use so as to derive from $x_M$ the position of the respective beam-defining edge. Each retroreflector 19 may accordingly be positioned at any convenient location along the upper side of the leaf so as to reflect illumination from the lamp 12 into the camera 13.

As an alternative to the localized retroreflectors 19 just described, the retroreflector means may extend along most or all of a leaf 8 so that only one edge (extending in the y-direction) of the retroreflector means is visible to the camera. In that case, however, the apparent position of the edge of the retroreflector is more liable to vary with the level of illumination from the lamp 12 than when the localized retroreflectors are provided.

The camera and the processing and storage means may also be operable to determine a desired cross-sectional shape for the radiation beam defined by further retroreflector means, that is retroreflector means other than those on the leaves 8. FIG. 3 illustrates two different ways in which this can be achieved. In the first, a further set of mutually contiguous leaves 20 is fitted in the head 7, two opposed leaves 20 being shown in FIG. 3. This further set of leaves 20 is similar to the set of leaves 8 of the main collimator for the radiation beam except that the further leaves are required only substantially to attenuate the illumination (in practice, they are likely to have negligible transmission for the illumination) and therefore may be lighter and more easily movable than the leaves 8 and that, being at a distance $D_3$ from the effective source of the radiation beam that is greater than the distance $D_1$ of the main collimator from the source, the leaves 20 are of greater width (their dimension in the y-direction of FIG. 2) so that the leaves 20 subtend the same angles at the source 10 or illuminating lamp 12 as the leaves 8, i.e. the respective widths are in the ratio $D_3/D_1$. When the further set of leaves 20 is to be used (the further set may be removably fitted in the head 7), the leaves 8 of the main collimator are adjusted to provide the maximum aperture so that an aperture with the cross-sectional shape of the illuminating beam is defined by the edges 20a of the further set of leaves 20. The positions of the further leaves 20 can be manually adjusted so that the boundary of the illuminated area on the surface 11 substantially matches an outline which is, for example, drawn on the skin of the patient. Each of the further leaves 20 is provided with respective further retroreflector means, in the example shown in FIG. 3 in the form of further retroreflectors 21 mounted on the leaves 20, whereby the positions of the aperture-defining edges 20a of the further leaves 20 can be determined by the camera 13 and the processing and storage means 17 in the same manner as with the main collimator, the positions then being stored by the processing and storage means 17. The further set of leaves 20 is then opened to provide its maximum aperture, or is completely removed from the head 7, and the stored edge positions are supplied to the control means 18 so that the edges 8a of the leaves 8 of the main collimator are adjusted to the same respective apparent positions previously occupied by the leaves 20: the desired region on the surface 11 will then be irradiated, since the transverse dimensions of the two sets of leaves 8, 20 subtend substantially the same respective angles at the source 10 (with reference, for example, to a central axis normal to the surface 11).

An alternative manner of determining the desired cross-sectional beam shape is simply to use a stick 22 carrying a retroreflector 23 at its tip and to trace the tip manually along the outline of the area which it is desired to irradiate.

The video camera 13 may be provided with an entrance diaphragm defining an aperture sufficient to allow only illumination from the lamp 12 reflected by the retroreflectors 19 (or 21) into the video camera 13. The provision of such an entrance diaphragm enables the contrast between the image of the retroreflector 19 (or 21) and the image formed by illumination reflected by scattering from other parts of the said illuminated area or field of view to be improved. Thus, in practice, the lamp 12 emits illumination having a finite cross-sectional area, that is a finite, if small, lateral extent, and a retroreflector at any location within the field of view of the camera 13 reflects illumination back to a corresponding focal region with a lateral extent corresponding approximately to the lateral extent of the illumination emitted by the lamp 12 so that, by defining the entrance aperture of the entrance diaphragm to correspond to the said small lateral extent of the illumination emitted from the lamp 12, most of the retroreflected illumination will pass through the entrance aperture whilst the amount of scattered non-retroreflected illumination entering the video camera 13 should be reduced. The entrance diaphragm may comprise the iris diaphragm of the video camera 13 stopped down to a diameter just before that at which the brightness of the retroreflected image begins to decrease so as to provide optimal enhancement of contrast. Alternatively, a separate contrast enhancing entrance diaphragm could be provided in front of or behind the lens of the video camera 13 for this purpose. The lamp 12 may comprise a compact filament halogen-quartz lamp. A lamp with a larger transverse filament spread could be used if a reflector and lens arrangement is provided to reduce the lateral extent of the illumination from the lamp 12.

For both the radiation-attenuating main collimator and the illumination-attenuating further collimator, it is not essential that the retroreflector means should be mounted directly on the leaves but only that the retroreflector means should be coupled to the leaves so that the positions of the retroreflector means are respectively representative of the positions of the edges of the leaves; the retroreflector means may for example be coupled to the leaves by respective levers.

Also, whilst in the embodiments described above a single localized retroreflector 19, 21 is provided for each member 8, 20, two or more retroreflectors spaced in a direction along the member transverse to the edge 8a, 20a may be provided and the outermost opposed edges of the set of retroreflectors used for determining the position of the edge 8a, 20a.

As mentioned above, a collimating arrangement embodying the invention may also be used with diagnostic X-rays rather than a beam of high-energy therapeutic radiation, typically in an X-ray simulator intended for use in conjunction with radiotherapy apparatus. Such a simulator is constructed to be analogous to the radiotherapy apparatus but to have a source of diagnostic X-rays at a location corresponding to the effective source of the high-energy beam. The simulator comprises an image-converting screen and video camera whereby the X-ray image of a portion of a patient can be displayed on a video screen. The leaves of the collimator can be adjusted so that the desired region of the patient is irradiated by the X-rays, and the positions of the edges of the leaves determined by the optical system. This information can then be fed to the radiotherapy apparatus so that the same region of the patient will be irradiated by the high-energy beam.

The retroreflector means used in embodiments of the invention may for example be individual corner cubes or may be portions of a commercially-available strip of retroreflective material such as "SCOTCHLITE" available in the UK from 3 M UK PLC.

While the invention has been described with reference to a collimating arrangement forming part of apparatus for radiotherapy or for diagnostic or simulation using conventional fluoroscopy, it may equally well be correspondingly employed in irradiation apparatus employed for other purposes such as for industrial or manufacturing use.

From reading the present disclosure, other modifications will be apparent to persons skilled in the art. Such modifications may involve other features which are already known in the design, manufacture and use of radiotherapy apparatus and collimating arrangements and component parts thereof and which may be used instead of or in addition to features already described herein. Although claims have been formulated in this application to particular combinations of features, it should be understood that the scope of the disclosure of the present application also includes any novel feature or any novel combination of features disclosed herein either explicitly or implicitly or any generalization thereof, whether or not it relates to the same invention as presently claimed in any claim and whether or not it mitigates any or all of the same technical problems as does the present invention. The applicants hereby give notice that new claims may be formulated to such features and/or combinations of such features during the prosecution of the present application or of any further application derived therefrom.

I claim:

1. A collimating arrangement for a beam of radiation, comprising a set of mutually contiguous members which substantially attenuate said radiation, means for adjusting the positions of the members so that edges thereof form an adjustable aperture for defining the cross-sectional shape of the beam, illuminating means for illuminating an area including the beam-defining edges of said members, and detecting means responsive to spatial variations in the intensity of illumination reaching the detecting means from said area for determining the positions of said beam-defining edges, wherein each of said members includes respective retroreflector means for reflecting illumination from the illuminating means into the detecting means substantially independently of the position in said area of said beam-defining edges of said members, and the detecting means are more responsive to the higher intensity of illumination reflected from the retroreflector means than reflected from adjacent regions in said area so as to detect the positions of the retroreflector means which are respectively representative of the positions of said edges of said members.

2. A collimating arrangement as claimed in claim 1, wherein each of the retroreflector means is of a limited extent having two opposed edges spaced-apart in a direction transverse to the respective beam-defining edge, and the detecting means are arranged to detect illumination reflected from said two edges of each retroreflector means in said area and to determine therefrom the position of the beam-defining edge of the respective member.

3. A collimating arrangement as claimed in claim 2, wherein the detecting means are arranged to determine from the illumination reflected from the said two opposed edges of each retroreflector means a midpoint between the said two opposed edges and to determine therefrom the position of the beam-defining edge of the respective member.

4. A collimating arrangement as claimed in claim 1, wherein each retroreflector means is mounted on the respective member.

5. A collimating arrangement as claimed in claim 1, wherein the detecting means includes an entrance diaphragm defining an entrance aperture sufficient to allow only illumination from the illumination means reflected by the retroreflector means into the detecting means.

6. A collimating arrangement as claimed in claim 5, wherein the detecting means comprises a video camera with an iris diaphragm of a camera lens forming the entrance diaphragm.

7. Irradiation apparatus comprising means for generating a beam of penetrating radiation and a collimating arrangement as claimed in claim 1, for collimating said beam.

8. Apparatus as claimed in claim 7, further comprising retroreflector means which define a desired cross-sectional beam shape, the detecting means being arranged to detect illumination from the illumination means reflected by the further retroreflector means to determine the desired cross-sectional beam shape defined by the further retroreflector means, means for storing the desired cross-sectional beam shape, and means for adjusting the position of said members so that the actual beam shape corresponds to the desired beam shape.

9. Apparatus as claimed in claim 8, further comprising a set of mutually contiguous further members which substantially attenuate illumination from the illuminating means, the positions of the further members being adjustable so that edges of the further members form an adjustable aperture defining the cross-sectional shape of the illuminating beam from the illuminating means, the lengths of said aperture-defining edges of the further members respectively subtending the same angles at the illuminating means as do the lengths of corresponding beam-defining edges of the members of the first-said set, each of said further members having a respective one of the further retroreflector means.

10. Apparatus as claimed in claim 8, comprising support means manually movable along a path for defining the desired beam shape wherein said further retroreflector means are carried on the support means.

* * * * *